US010254211B2

(12) United States Patent
Niiyama et al.

(10) Patent No.: US 10,254,211 B2
(45) Date of Patent: Apr. 9, 2019

(54) FLOW CELL, PARTICLE ANALYSIS APPARATUS AND PARTICLE ANALYSIS METHOD

(71) Applicant: Nihon Kohden Corporation, Tokyo (JP)

(72) Inventors: Yoshihiro Niiyama, Tokyo (JP); Maki Suezawa, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 105 days.

(21) Appl. No.: 15/409,698

(22) Filed: Jan. 19, 2017

(65) Prior Publication Data
US 2017/0212031 A1 Jul. 27, 2017

(30) Foreign Application Priority Data

Jan. 22, 2016 (JP) ................. 2016-010970

(51) Int. Cl.
*G01N 15/10* (2006.01)
*G01N 15/14* (2006.01)
*G01N 15/12* (2006.01)

(52) U.S. Cl.
CPC ..... *G01N 15/1031* (2013.01); *G01N 15/1404* (2013.01); *G01N 15/1056* (2013.01);
(Continued)

(58) Field of Classification Search
CPC .......... G01N 15/1031; G01N 15/1404; G01N 15/1056; G01N 15/1006; G01N 15/1254
See application file for complete search history.

(56) References Cited

U.S. PATENT DOCUMENTS 4,090,128 A 5/1978 Simpson et al.
5,245,318 A * 9/1993 Tohge ................ G01N 15/1404
324/71.4
(Continued)

FOREIGN PATENT DOCUMENTS

EP 0435166 A2 7/1991
EP 0478392 A2 4/1992
(Continued)

OTHER PUBLICATIONS

European Search Report for Application No. 17152412.7, dated Jun. 26, 2017.

*Primary Examiner* — Tung X Nguyen
*Assistant Examiner* — Dominic Hawkins
(74) *Attorney, Agent, or Firm* — Drinker Biddle & Reath LLP

(57) ABSTRACT

A flow cell includes a first layer, a second layer, and a third layer. The first layer includes a first flow path and a first electrode. The second layer includes a second flow path and a second electrode. The third layer is formed between the first layer and the second layer, and includes a first connection hole connecting the first flow path and the second flow path. The first electrode is disposed in the first flow path at a first side opposite to a second side where a sample is provided to the first flow path with respect to the first connection hole. The second electrode is disposed in the second flow path at a third side opposite to a fourth side where a fluid is discharged from the second flow path with respect to the first connection hole.

9 Claims, 11 Drawing Sheets

(52) U.S. Cl.
CPC ................ *G01N 2015/1006* (2013.01); *G01N 2015/1254* (2013.01)

(56) References Cited

U.S. PATENT DOCUMENTS

| | | | | |
|---|---|---|---|---|
| 5,446,532 A * | 8/1995 | Yamazaki | ......... | G01N 15/1459 356/338 |
| 5,656,501 A * | 8/1997 | Yedgar | ............... | G01N 15/1404 356/244 |
| 6,365,106 B1 * | 4/2002 | Nagai | ................ | G01N 15/1404 356/246 |
| 6,592,821 B1 * | 7/2003 | Wada | ................. | B01F 13/0062 422/50 |
| 7,311,476 B2 * | 12/2007 | Gilbert | .............. | B01L 3/502776 406/198 |
| 8,298,722 B2 * | 10/2012 | Chou | ................. | H01M 4/8889 429/514 |
| 2005/0123450 A1 * | 6/2005 | Gilbert | .............. | B01L 3/502776 422/81 |
| 2011/0162439 A1 * | 7/2011 | Ayliffe | .............. | B01L 3/502715 73/61.71 |
| 2012/0107805 A1 * | 5/2012 | Neas | ..................... | B01L 3/0296 435/6.1 |
| 2014/0170697 A1 * | 6/2014 | Sharpe | ............... | G01N 15/1436 435/30 |
| 2014/0315238 A1 * | 10/2014 | Farrell | ............... | G01N 15/1404 435/29 |
| 2015/0024373 A1 * | 1/2015 | Xia | ....................... | F04B 43/095 435/2 |
| 2015/0072350 A1 * | 3/2015 | Matsui | ............... | G01N 15/1404 435/6.12 |
| 2015/0114093 A1 * | 4/2015 | Appleyard | ......... | G01N 15/1404 73/61.59 |
| 2015/0125768 A1 * | 5/2015 | Mosso | ................ | H01M 8/0273 429/418 |
| 2015/0176070 A1 * | 6/2015 | Ota | ........................ | G01N 21/05 506/38 |
| 2016/0082432 A1 * | 3/2016 | Katsumoto | ............ | G01N 27/02 204/643 |

FOREIGN PATENT DOCUMENTS

| | | |
|---|---|---|
| EP | 2995961 A1 | 3/2016 |
| JP | 2002277380 A | 9/2002 |

* cited by examiner

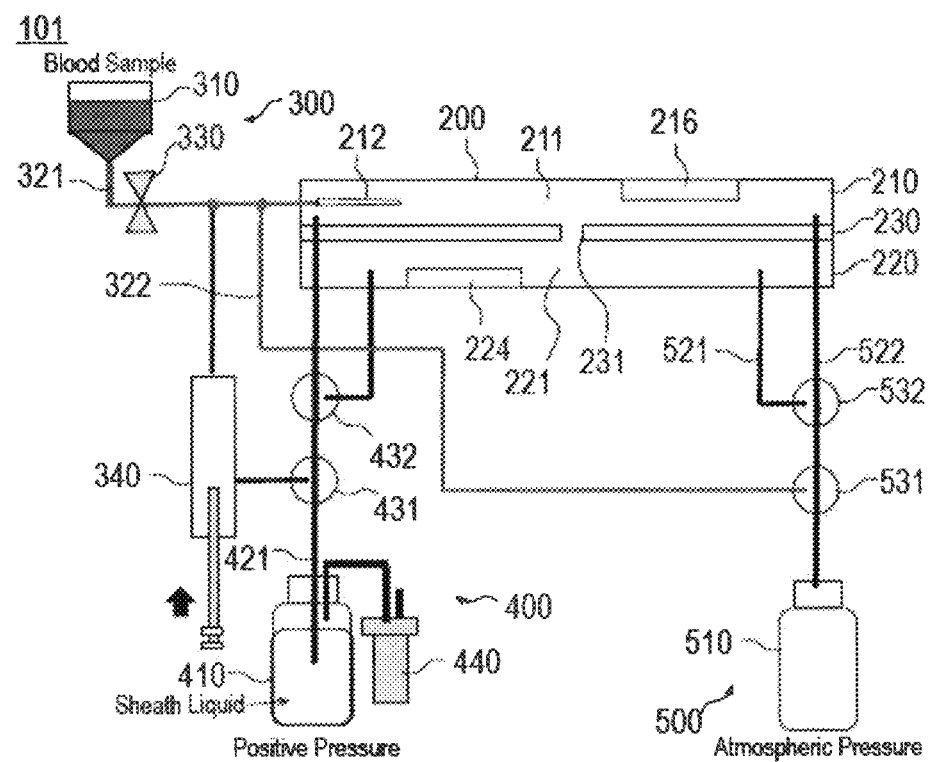

FLOW CELL, PARTICLE ANALYSIS APPARATUS AND PARTICLE ANALYSIS METHOD

CROSS-REFERENCE TO RELATED APPLICATION

This application claims priority to Japanese Patent Application No. 2016-010970 filed on Jan. 22, 2016, the contents of which are incorporated herein by reference.

BACKGROUND

The present subject matter relates to a flow cell, a particle analysis apparatus, and a particle analysis method.

At medical scenes, it has been desired to realize a small blood test apparatus with which a healthcare worker can quickly perform blood test for a subject (patient). When the sizes of blood test apparatuses are reduced to achieve a higher degree of portability, it is expected to quickly perform blood tests of many patients in medical organizations such as general hospitals and clinics. In particular, among blood tests, an inspection for counting blood cells such as erythrocytes, leukocytes, and platelets in blood is an inspection that is carried out frequently at medical organizations, and therefore, it is important to develop a small hematology analyzer.

Among such hematology analyzers, for example, a hematology analyzer of an electric resistance type introduces a blood sample of a patient into a chamber of a hematology sensor unit and counts blood cells on the basis of a change in an electric resistance when the blood cells pass through an aperture. However, in the conventional hematology analyzer, the blood sample may contaminate the chamber, or bubbles accumulated around the aperture may change the electric resistance, so that this may affect the accuracy of blood cell count.

In relation to this, in order to prevent the contamination and bubbles in the chamber from affecting the accuracy, disposable hematology sensor unit has been developed (for example, Japanese Patent Publication No. 2002-277380). However, in such hematology analyzer, components for constituting the disposable sensor unit are expensive, and therefore, it is difficult to put the hematology analyzer into practice.

Therefore, the present subject matter provides a flow cell, a particle analysis apparatus, and a particle analysis method that can prevent or suppress the contamination and bubbles in the chamber from affecting the accuracy.

SUMMARY

A flow cell according to the present subject matter includes a first layer, a second layer, and a third layer. The first layer includes a first flow path and a first electrode. The second layer includes a second flow path and a second electrode. The third layer is formed between the first layer and the second layer, and includes a first connection hole connecting the first flow path and the second flow path. The first electrode is disposed in the first flow path at a side opposite to a side where a sample is supplied to the first flow path with respect to the first connection hole. The second electrode is disposed in the second flow path at a side opposite to a side where a fluid is discharged from the second flow path with respect to the first connection hole.

The particle analysis apparatus includes a flow cell, a sample supply unit, and an analysis unit. The fluid injection portion injects a fluid including particles, which are to be counted, to the first flow path. The analysis unit is connected to the first electrode and the second electrode, and analyzes the particles, which are to be counted, on the basis of a resistance value between the first electrode and the second electrode.

A particle analysis method includes a step (a) of supplying a sheath liquid from one end of a first flow path of a first layer and discharging the sheath liquid to the other end, a step (b) of supplying the sheath liquid from one end of a second flow path of a second layer and discharging the sheath liquid to the other end, a step (c) of closing the first flow path at a side where the sheath liquid is discharged, closing the second flow path at a side where the sheath liquid is supplied, supplying the sheath liquid to the first flow path, and discharges the sheath liquid via a first connection hole from the second flow path, and a step (d) of injecting a fluid to the first flow path at a side where the sheath liquid is supplied, and counting particles included in the fluid that passes through the first connection hole. The first connection hole is formed in a third layer between the first layer and the second layer, and connects the first flow path and the second flow path.

The objects, features, and characteristics of the present subject matter other than those set forth above will become apparent from the description given herein below with reference to preferred embodiments illustrated in the accompanying drawings.

BRIEF DESCRIPTION OF THE DRAWINGS

FIG. 7 is a schematic diagram illustrating a modification of the first embodiment of the present subject matter;

DETAILED DESCRIPTION

Figure 1:
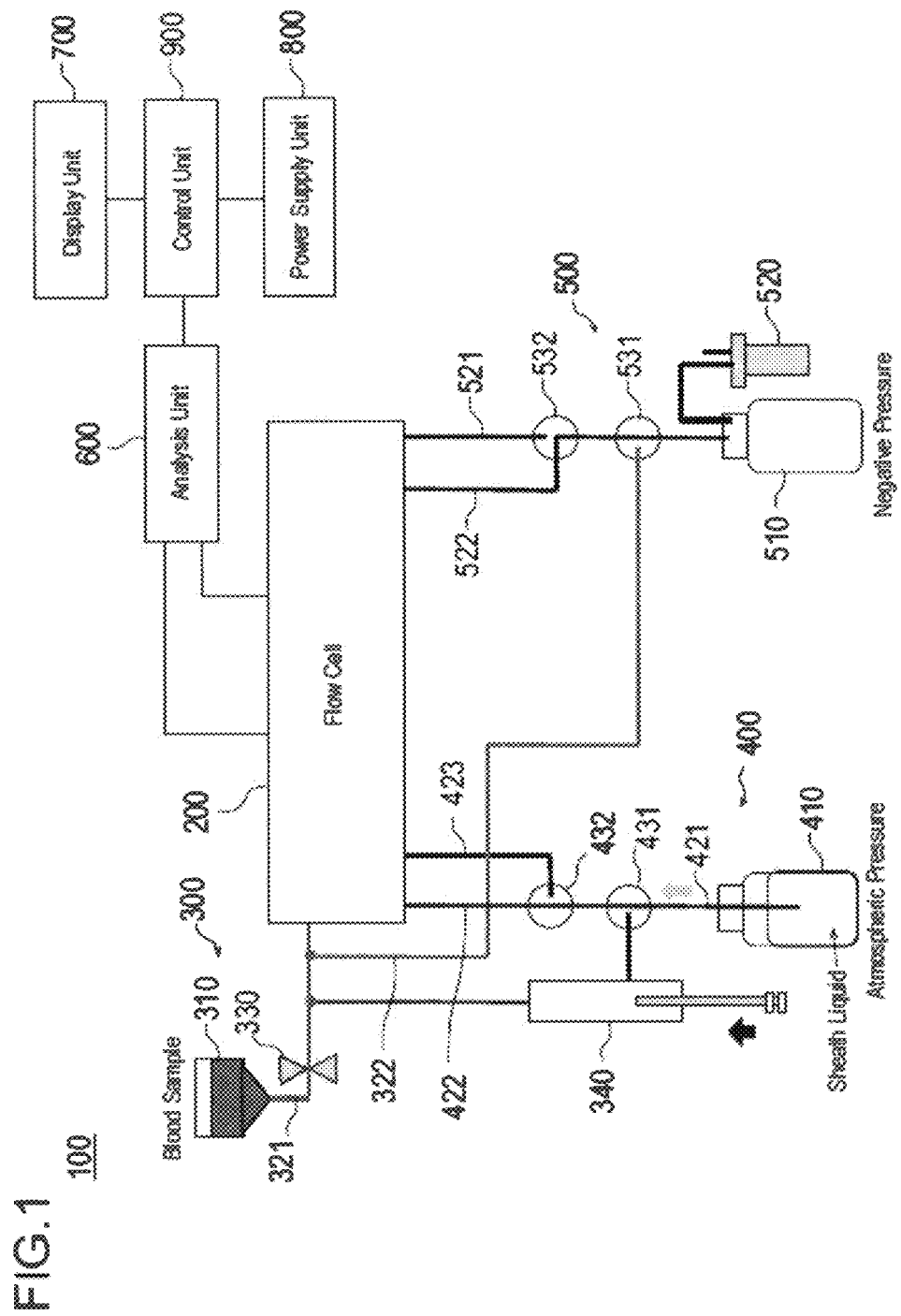
FIG. 1 is a block diagram illustrating a schematic configuration of a particle analysis apparatus according to a first embodiment of the present subject matter.

Embodiments of a flow cell, a particle analysis apparatus, and a particle analysis method according to the present subject matter will be hereinafter explained with reference to drawings. In the drawings, the same members are denoted with the same reference numerals. The dimensional ratios in the drawings are exaggerated for the sake of explanation, and may be different from actual ratios.

First Embodiment

FIG. 1 is a block diagram illustrating a schematic configuration of a particle analysis apparatus 100 according to the first embodiment of the present subject matter. The particle analysis apparatus 100 is an apparatus for analyzing particles included in a sample. Hereinafter, for example, a case for measuring the number of blood cells included in the blood sample will be explained.

<Configuration of Particle Analysis Apparatus 100>

As shown in FIG. 1, the particle analysis apparatus 100 can include a flow cell 200, a sample supply unit 300, a sheath liquid supply unit 400, a waste liquid collection unit 500, an analysis unit 600, a display unit 700, a power supply unit 800, and a control unit 900.

The flow cell 200 outputs information about the size of each blood cell included in the blood sample to the analysis unit 600 as a resistance value. More specifically, the flow cell 200 includes a pair of electrodes, and the resistance value between the pair of electrodes changes in accordance with the size of each blood cell included in the blood sample supplied to the flow cell 200. The details of the configuration of the flow cell 200 will be explained later.

The sample supply unit 300 supplies the blood sample to the flow cell 200. The sample supply unit 300 includes a sample chamber 310, pipes 321, 322, a sample supply valve 330, and a sample pump 340. The sample chamber 310 is a chamber for holding the blood sample, and is connected via the sample supply valve 330 to the flow cell 200 with the pipe 321. The sample chamber 310 is also connected via the sample supply valve 330 to the waste liquid collection unit 500 with the pipe 322. The pipe 322 is used when, for example, a blood sample, which is no longer needed, in the sample chamber 310 is directly discharged to the waste liquid collection unit 500. The blood sample is a liquid obtained by diluting the blood collected from a patient by a factor appropriate for the measurement with the dilution liquid, and a hemolyzed blood.

The sample supply valve 330 is, for example, a pinch valve, and the sample supply valve 330 is provided between the sample chamber 310 and the flow cell 200, and is configured to open and close the valve in accordance with a command of the control unit 900. When the sample supply valve 330 is open, the blood sample is supplied from the sample chamber 310 to the flow cell 200 and the waste liquid collection unit 500. On the other hand, when the sample supply valve 330 is closed, the supply of the blood sample from the sample chamber 310 to the flow cell 200 and the waste liquid collection unit 500 is cut off. Therefore, the control unit 900 can adjust the timing with which the blood sample is supplied from the sample chamber 310 to the flow cell 200 and the waste liquid collection unit 500.

The sample pump 340 (for example, syringe pump) applies pressure to the blood sample of the pipe 321. The sample pump 340 is connected to the sheath liquid supply unit 400 and the pipe 321. The sample pump 340 introduces the sheath liquid from the sheath liquid supply unit 400 in accordance with a command of the control unit 900, discharges the sheath liquid to the pipe 321, and applies a predetermined pressure to the blood sample of the pipe 321. Therefore, the control unit 900 can adjust the amount of the blood sample supplied from the sample chamber 310 to the flow cell 200. Instead of introducing the sheath liquid from the sheath liquid supply unit 400 to the sample pump 340, the dilution liquid may be configured to be separately supplied to the sample pump 340.

The sheath liquid supply unit 400 supplies the sheath liquid to the flow cell 200. The sheath liquid supply unit 400 can include a sheath liquid chamber 410, a pipe 421, a first supply valve 431, and a second supply valve 432.

The sheath liquid chamber 410 holds the sheath liquid (for example, physiological salt solution). The first supply valve 431 switches the destination of the supply of the sheath liquid in the sheath liquid chamber 410 to any one of the sample pump 340 and the flow cell 200. The second supply valve 432 switches the destination of the supply of the sheath liquid to any one of the pipe 422 and the pipe 423. As explained later, the pipe 422 and the pipe 423 are connected to a sheath liquid injection portion of the flow cell 200. The first supply valve 431 and the second supply valve 432 are, for example, three-way electromagnetic valves, and are controlled by the control unit 900.

The waste liquid collection unit 500 collects the waste liquid from the flow cell 200. The waste liquid collection unit 500 can include a waste liquid collection chamber 510, a suction pump 520, a first collection valve 531, and a second collection valve 532.

The waste liquid collection chamber 510 is a chamber for accumulating the waste liquid from the flow cell 200. The suction pump 520 sucks the content of the waste liquid collection chamber 510. The suction pump 520 sucks the content of the waste liquid collection chamber 510 so as to cause the inside of the waste liquid collection chamber 510 to have a negative pressure with respect to the atmospheric pressure. When the inside of the waste liquid collection chamber 510 is caused to have a negative pressure with respect to the atmospheric pressure, the sheath liquid of the sheath liquid supply unit 400 having the atmospheric pressure is sucked and supplied to the flow cell 200. In such particle analysis apparatus of the negative pressure drive, the number of components can be reduced, and accordingly, the cost can be suppressed, as compared with the positive pressure drive.

The first collection valve 531 selects any one of the blood sample supplied from the pipe 322 of the sample supply unit 300 and the waste liquid from the flow cell 200, and discharges the blood sample or the waste liquid to the waste liquid collection chamber 510. The second collection valve 532 selects any one of the pipe 521 and the pipe 522, and discharges the waste liquid from the flow cell 200 to the first collection valve 531. As described later, the pipe 521 and the pipe 522 are connected to a discharge portion of the flow cell 200. The first collection valve 531 and the second collection valve 532 are, for example, three-way electromagnetic valves, and are controlled by the control unit 900.

The analysis unit 600 counts the blood cells included in the blood sample. The analysis unit 600 includes a constant current source and a voltmeter, and counts particular blood cells included in the blood sample on the basis of an electric resistance method. The analysis unit 600 causes a constant current to pass between the pair of electrodes of the flow cell 200, and obtains a voltage pulse according to a change in the resistance value (which may be hereinafter also referred to as "blood cell pulse") when the blood cells pass through the aperture. The peak value of the blood cell pulse is known to be proportional to the volume of the blood cell. The analysis unit 600 measures the number of blood cell pulses of the predetermined peak value corresponding to the particular blood cell, and calculates the number of particular blood cells included in the blood sample. The particular blood cell is, for example, erythrocyte, platelet, and leukocyte.

The analysis unit 600 is also configured to be able to measure measurement items other than erythrocyte, leukocyte, and platelet, for example, hemoglobin concentration (HGB), hematocrit value (HCT), Mean Corpuscular Volume (MCV), Mean Corpuscular Hemoglobin (MCH), lymphocytes percentage (LY %), monocyte percentage (MO %), granulocyte percentage (GR %), lymphocytes (LY), monocyte (MO), granulocyte (GR).

The display unit 700 includes a display, and displays the number of blood cells calculated by the analysis unit 600.

The power supply unit 800 provides a power supply to the sample supply unit 300, the sheath liquid supply unit 400, the waste liquid collection unit 500, the analysis unit 600, the display unit 700, and the control unit 900.

The control unit 900 controls the sample supply unit 300, the sheath liquid supply unit 400, the waste liquid collection unit 500, the analysis unit 600, the display unit 700, and the power supply unit 800. The control unit 900 can include a computation processing unit and a storage unit. The computation control unit executes a control program stored in a storage unit. The control program is configured to cause the particle analysis apparatus 100 to execute a particle analysis method. The particle analysis method will be explained later.

<Configuration of Flow Cell 200>

Figure 2:
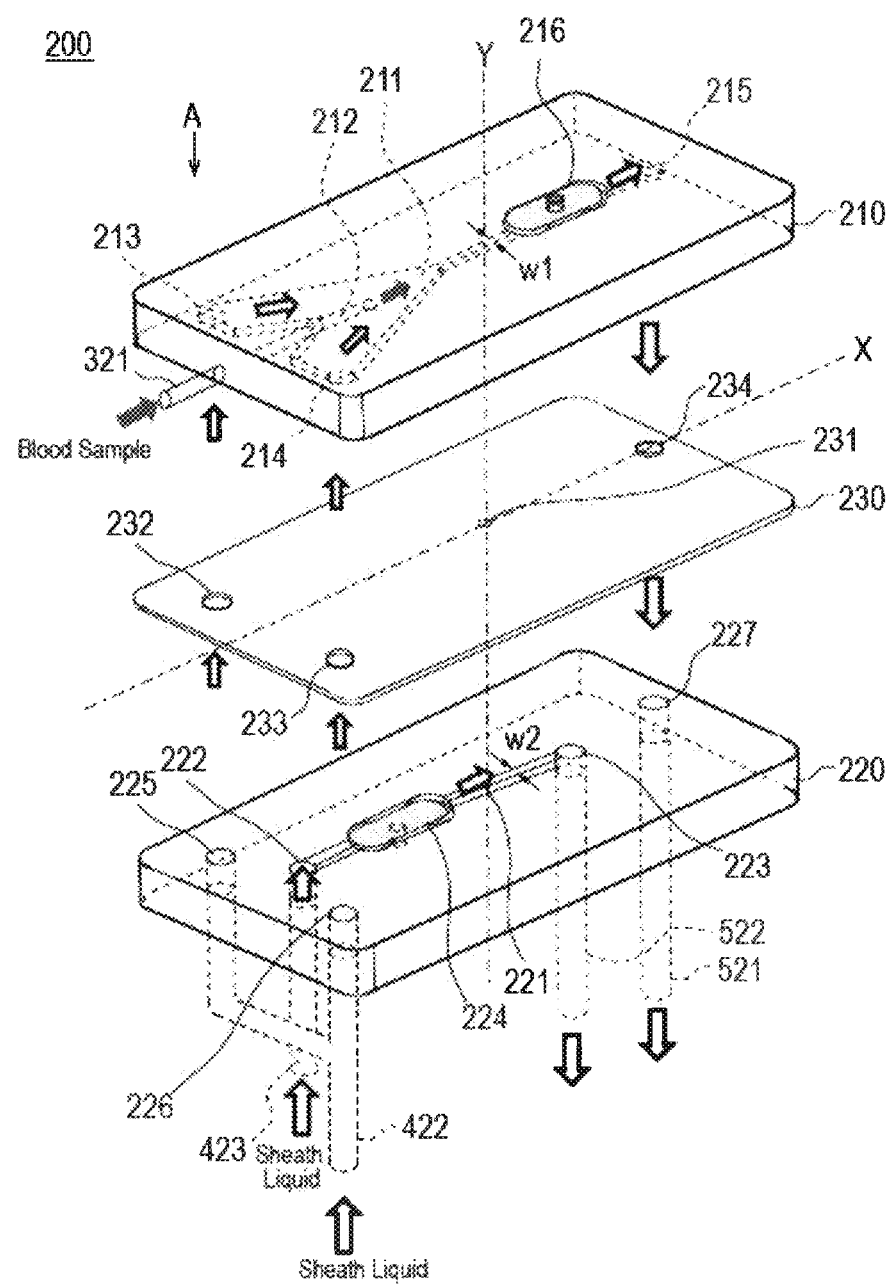
FIG. 2 is an exploded oblique perspective view illustrating a configuration of the flow cell illustrated in FIG. 1.

FIG. 2 is an exploded oblique perspective view illustrating a configuration of the flow cell 200 as shown in FIG. 1. The flow cell 200 can include a first layer 210, a second layer 220, and a third layer 230. In FIG. 2, a surface that can be seen from direction A is defined as an upper surface, and a surface that can be seen from a direction opposite to the direction A is defined as a lower surface. For example, the flow cell 200 can be made by forming patterns such as recessed portions and holes serving as flow paths in three plate-shaped resins and laminating and adhering the three plate-shaped resins. Publicly-known techniques such as etching processing and laser processing can be used in order to form the pattern. As described above, the flow cell 200 has a simple laminated structure, and therefore, the flow cell 200 can be made into a small size, a light weight, and at a low cost. It should be noted that the flow cell 200 may also be made with glass and ceramics.

The first layer 210 can include a first flow path 211, a sample injection portion 212, sheath liquid injection portions 213, 214, a discharge portion 215, and a first electrode 216.

The first flow path 211 is a very small flow path for introducing a fluid from the sample injection portion 212 and the sheath liquid injection portions 213, 214 to the discharge portion 215. When the recessed portion formed on the lower surface side of the first layer 210 and the upper surface of the third layer 230 are brought into contact with each other, the first flow path 211 is configured to have a rectangular cross section. An internal dimension w1 of the first flow path 211 is preferably equal to or less than, for example, 1 mm square. The recessed portion of the first layer 210 is formed to have a Y shape when the first layer 210 is seen from the lower surface side in the planar view. The sheath liquid injection portions 213, 214 and the discharge portion 215 are disposed at both end portions of the first flow path 211. The sample injection portion 212 is disposed at a position where the sheath liquid flowing from each of the sheath liquid injection portions 213, 214 are merged.

The sample injection portion 212 injects the blood sample supplied from the sample supply unit 300 into the first flow path 211. The sample injection portion 212 is formed at the lower surface side of the first layer 210, and includes a nozzle. The blood sample supplied from the pipe 321 is discharged from the nozzle to be injected into the first flow path 211.

The first electrode 216 is one of the pair of electrodes, and is connected to the analysis unit 600. The first electrode 216 is disposed at the side of the discharge portion 215 of the first flow path 211, i.e., in the first flow path 211 at a side opposite to the side where the blood flows into the first flow path 211 with respect to an aperture (first connection hole) 231 explained later. The first electrode 216 is preferably disposed in the first flow path 211 at a position closer to the aperture 231. The first electrode 216 includes a lead portion exposed to the upper surface of the first layer 210. The lead portion is connected via a wire to the analysis unit 600.

The pipe 422 is branched into two pipes, which are detachably connected to the sheath liquid injection portions 213, 214, respectively. The pipe 521 is detachably connected to the discharge portion 215.

The second layer 220 can include a second flow path 221, a sheath liquid injection portion 222, a discharge portion 223, a second electrode 224, sheath liquid transport holes 225, 226, and a waste liquid transport hole 227.

The second flow path 221 is a very small flow path for introducing a fluid from the sheath liquid injection portion 222 to the discharge portion 223. When the recessed portion formed on the upper surface side of the second layer 220 and the lower surface of the third layer 230 are brought into contact with each other, the second flow path 221 is configured to have a rectangular cross section. The cross section may be in a semicircular shape or round shape. The internal dimension w2 of the second flow path 221 is preferably equal to or less than, for example, 1 mm square. The second flow path 221 is formed to be in parallel with the first flow path 211. When the second flow path 221 is formed to be in parallel with the first flow path 211, the size of the flow cell 200 can be reduced.

The second electrode 224 is the other of the pair of electrodes, and is connected to the analysis unit 600. The second electrode 224 is disposed at the side of the sheath liquid injection portion 222 of the second flow path 221, i.e., in the second flow path 221 at a side opposite to the side where the fluid flows out from the second flow path 221 with respect to the aperture 231 explained later. The second electrode 224 is preferably disposed in the second flow path 221 at a position closer to the aperture 231. The second electrode 224 includes a lead portion exposed to the lower surface of the second layer 220. The lead portion is connected via a wire to the analysis unit 600.

The sheath liquid transport holes 225, 226 are penetration holes in which the pipe 422 passes through. The pipe 422 transports the sheath liquid from the second layer 220 to the first layer 210. The waste liquid transport hole 227 is a penetration hole in which the pipe 521 passes through. The pipe 521 transports the waste liquid from the first layer 210 to the second layer 220.

The pipe 423 is detachably connected to the sheath liquid injection portion 222. The pipe 522 is detachably connected to the discharge portion 223.

As described above, the pipes 422, 423, 521, and 522 are detachably connected to the flow cell 200, and therefore, the flow cell 200 can be easily attached to and detached from the main body of the particle analysis apparatus 100. As described later, the flow cell 200 is not disposable that can be used for a single use (disposable type), and may be repeatedly used for any number of times. However, the flow cell 200 is preferably replaced after the flow cell 200 is used for a predetermined number of times, so that the flow cell 200 is maintained in a clean state, and the measurement precision is maintained at a constantly high level. The flow cell 200 can be easily attached to and detached from the main body of the particle analysis apparatus 100. Therefore, the flow cell 200 can be replaced with a regular interval.

The first electrode 216 and the second electrode 224 are not particularly limited, but the first and second electrodes 216, 224 are made of the same metal, so that an occurrence of a potential difference can be suppressed. Therefore, the electrode material is preferably a platinum electrode. However, for example, the electrode material may also be a titanium-platinum electrode and a cheap carbon-carbon electrode. When such electrode materials are used, the cost of the electrode materials can be reduced.

The third layer 230 is formed between the first layer 210 and the second layer 220, and includes an aperture 231, a sheath liquid transport holes 232, 233, and a waste liquid transport hole 234. The aperture 231 is a connection hole for connecting the first flow path 211 and the second flow path 221 in the middle thereof. The size of the aperture 231 is preferably about 1 to 100 μm, but the size of the aperture 231 is not limited to this range of size. The sheath liquid transport holes 232, 233 are penetration holes through which the pipe 422 penetrates. The waste liquid transport hole 234 is a penetration hole through which the pipe 521 penetrates.

<Particle Analysis Method>

Figure 3:
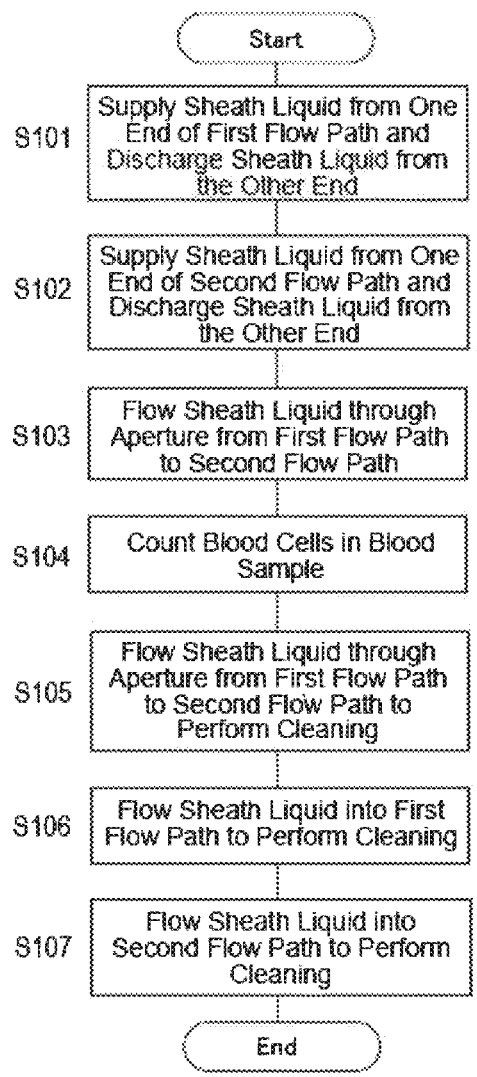
FIG. 3 is a flowchart illustrating an example of a particle analysis method according to the first embodiment of the present subject matter.

FIG. 3 is a flowchart illustrating an example of a particle analysis method according to the present embodiment. FIG. 4A to FIG. 4G are schematic diagrams illustrating operations corresponding to each step of the flowchart shown in FIG. 3. FIG. 4A to FIG. 4G illustrate a cross section of the flow cell 200 taken along XY plane of FIG. 2.

Figure 4A:
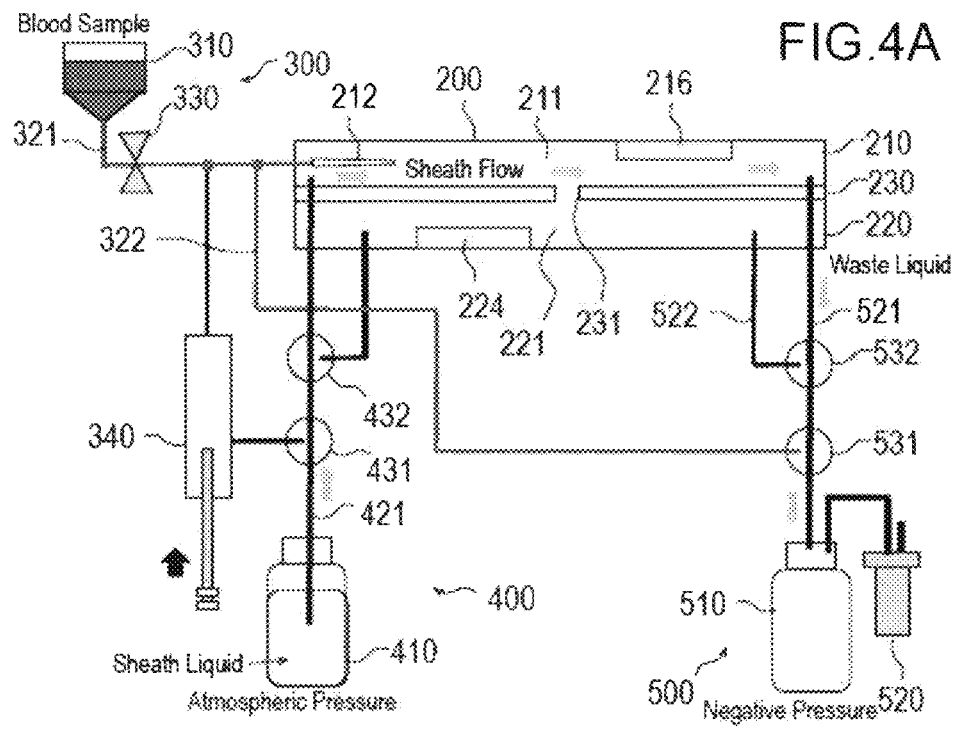
FIG. 4A is a schematic diagram illustrating an operation corresponding to each step of the flowchart shown in FIG. 3.

As shown in FIG. 3 and FIG. 4A, first, the sheath liquid is supplied from one end of the first flow path 211, and the sheath liquid is discharged from the other end (step S101). The control unit 900 controls the sample supply unit 300, the sheath liquid supply unit 400, and the waste liquid collection unit 500 to supply the sheath liquid to the first flow path 211 and collects the waste liquid.

More specifically, at the side of the supply unit, the sample supply valve 330 is closed, and the supply of the blood sample is cut off. The first supply valve 431 and the second supply valve 432 are controlled, so that a path is established to supply the sheath liquid from the sheath liquid chamber 410 via the sheath liquid injection portions 213, 214 to the first flow path 211.

On the other hand, at the side of the collection unit, the first collection valve 531 and the second collection valve 532 are controlled, so that a path is established to discharge the sheath liquid from the first flow path 211 via the discharge portion 215 to the waste liquid collection chamber 510. Subsequently, the suction pump 520 is activated to suck the content (air) in the waste liquid collection chamber 510. When the content in the waste liquid collection chamber 510 is sucked, the inside of the waste liquid collection chamber 510 changes to a negative pressure with respect to the atmospheric pressure, and accordingly, the sheath liquid in the sheath liquid chamber 410 flows into the sheath liquid injection portions 213, 214, and flows through the first flow path 211, and then, the sheath liquid passes through the discharge portion 215 to be accumulated in the waste liquid collection chamber 510. Since the first flow path 211 has a very small structure, the first flow path 211 has a small capacity, so that the first flow path 211 is filled with a small amount of sheath liquid in a short period of time. Therefore, as compared with conventional chambers, the time for supplying the sheath liquid can be reduced.

When the sheath liquid passes through the first flow path 211 before the number of blood cells in the blood sample is counted, smears such as blood and bubbles can be removed even if the smears and the blood are attached to the first flow path 211.

Figure 4B:
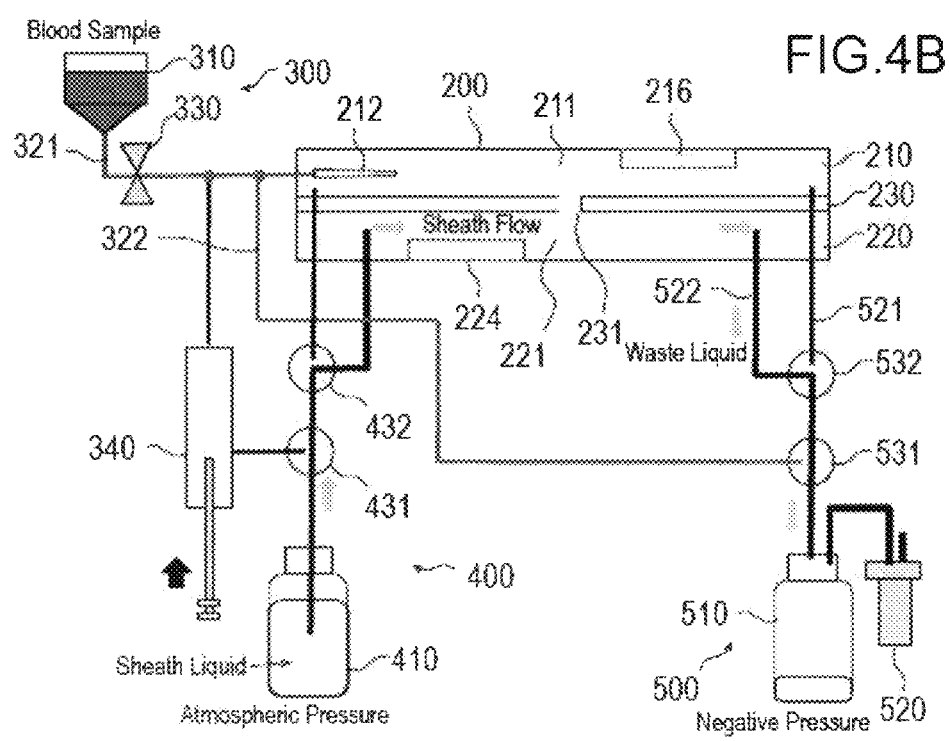
FIG. 4B is a schematic diagram connected subsequently to FIG. 4A.

Subsequently, as shown in FIG. 4B, the sheath liquid is supplied from one end of the second flow path 221, and is discharged from the other end (step S102). The control unit 900 controls the sample supply unit 300, the sheath liquid supply unit 400, and the waste liquid collection unit 500 to supply the sheath liquid to the second flow path 221 and collects the waste liquid.

More specifically, at the side of the supply unit, the sample supply valve 330 is closed, and the supply of the blood sample is cut off. The first supply valve 431 and the second supply valve 432 are controlled, so that a path is established to supply the sheath liquid from the sheath liquid chamber 410 via the sheath liquid injection portion 222 to the second flow path 221.

On the other hand, at the side of the collection unit, the first collection valve 531 and the second collection valve 532 are controlled, so that a path is established to discharge the sheath liquid from the second flow path 221 via the discharge portion 223 to the waste liquid collection chamber 510. Subsequently, the suction pump 520 is activated, and the contents (air/sheath liquid) of the waste liquid collection chamber 510 are sucked. When the content in the waste liquid collection chamber 510 is sucked, the inside of the waste liquid collection chamber 510 changes to a negative pressure with respect to the atmospheric pressure, and accordingly, the sheath liquid in the sheath liquid chamber 410 flows into the sheath liquid injection portion 222, and flows through the second flow path 221, and then, the sheath liquid passes through the discharge portion 223 to be accumulated in the waste liquid collection chamber 510. The sheath liquid filling the first flow path 211 is shut off by the second collection valve 532, so that the sheath liquid is not discharged to the waste liquid collection chamber 510, and accordingly, the sheath liquid is held in the first flow path 211. Since the second flow path 221 has a very small structure, the second flow path 221 has a small capacity, so that the second flow path 221 is filled with a small amount of sheath liquid in a short period of time. Therefore, as compared with conventional chambers, the time for supplying the sheath liquid can be reduced.

When the sheath liquid passes through the second flow path 221 before the number of blood cells in the blood sample is counted, smears such as blood and bubbles can be removed even if the smears and the blood are attached to the second flow path 221.

Figure 4C:
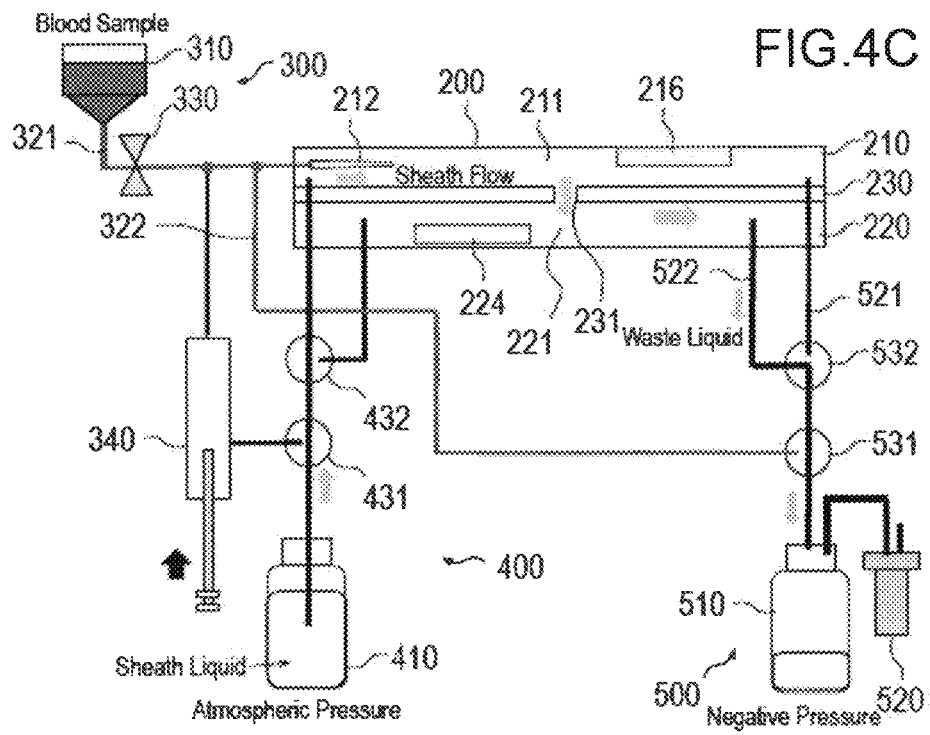
FIG. 4C is a schematic diagram connected subsequently to FIG. 4B.

Subsequently, the sheath liquid flows through the aperture 231 from the first flow path 211 to the second flow path 221 (step S103). As shown in FIG. 4C, the control unit 900 controls the sample supply unit 300, the sheath liquid supply unit 400, and the waste liquid collection unit 500 to supply the sheath liquid to the first flow path 211. The sheath liquid supplied to the first flow path 211 flows through the aperture 231 from the first flow path 211 to the second flow path 221. Then, the waste liquid collection unit 500 collects the waste liquid.

More specifically, at the side of the supply unit, the sample supply valve 330 is closed, and the supply of the blood sample is cut off. Then, the first supply valve 431 and the second supply valve 432 are controlled, so that a path is established to supply the sheath liquid from the sheath liquid chamber 410 via the sheath liquid injection portions 213, 214 to the first flow path 211. The path to supply the sheath liquid from the sheath liquid chamber 410 to the second flow path 221 is cut off by the second supply valve 432. More specifically, at the side where the sheath liquid is supplied, the second flow path 221 is closed.

On the other hand, at the side of the collection unit, the first collection valve 531 and the second collection valve 532 are controlled, so that the sheath liquid flows through the aperture 231 to the second flow path 221. A path is established to allow the waste liquid to flow from the second flow path 221 via the discharge portion 223 to the waste liquid collection chamber 510. Subsequently, when the suction pump 520 is activated, the contents (air/sheath liquid) in the waste liquid collection chamber 510 are sucked, and the sheath liquid in the sheath liquid chamber 410 flows into the sheath liquid injection portions 213, 214, and flows through the first flow path 211. Then, the sheath liquid flows through the aperture 231 into the second flow path 221, and the sheath liquid is accumulated in the waste liquid collection chamber 510. Therefore, when the sheath liquid passes through the aperture 231 from the first flow path 211 to the second flow path 221 before the blood cells in the blood sample are measured, smears such as blood can be removed even if the smears are attached to the aperture 231.

Subsequently, the blood cells in the blood sample are counted (step S104). The control unit 900 controls the sample supply unit 300, the sheath liquid supply unit 400, the waste liquid collection unit 500, and the analysis unit 600 to count the blood cells in the blood sample supplied to the flow cell 200 by the sample supply unit 300.

Figure 4D:
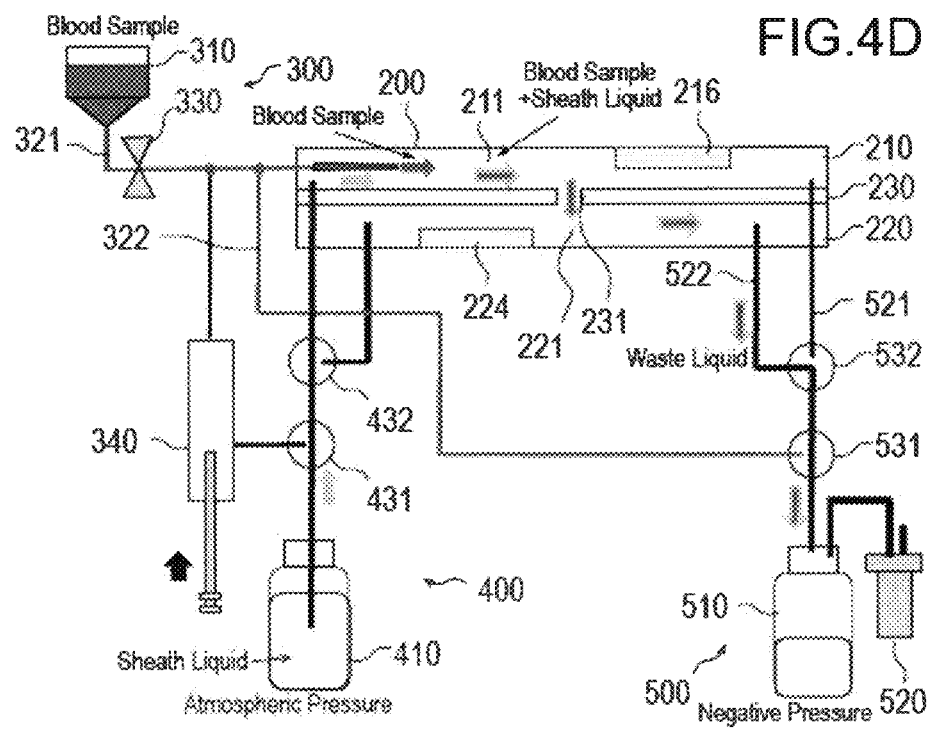
FIG. 4D is a schematic diagram connected subsequently to FIG. 4C.

As shown in FIG. 4D, the sheath liquid is supplied from the sheath liquid chamber 410 to the first flow path 211, and the blood sample is injected into the first flow path 211 while the path to allow a flow through the aperture 231 to the second flow path 221 is established.

More specifically, the sample supply valve 330 is opened, and the blood sample of the pipe 321 is pressurized by the sample pump 340, and the blood sample is injected from the nozzle of the sample injection portion 212 into the first flow path 211. The blood sample injected into the first flow path 211 flows through the first flow path 211 while the blood sample is wrapped by the sheath liquid injected from the sheath liquid injection portions 213, 214. In the present embodiment, since the first flow path 211 has a very small structure, the first flow path 211 has a small capacity, so that the amount of the blood sample can be reduced as compared with the conventional case.

On the other hand, the path from the first flow path 211 via the discharge portion 215 to the waste liquid collection chamber 510 is cut off by the second collection valve 532. More specifically, at the side where the blood sample and the sheath liquid are discharged, the first flow path 211 is closed. The path for supplying the sheath liquid from the sheath liquid chamber 410 to the second flow path 221 is cut off by the second supply valve 432. More specifically, at the side where the sheath liquid is supplied, the second flow path 221 is closed. Therefore, the sheath liquid and the blood sample flow through the aperture 231 into the second flow path 221, and the sheath liquid passes through the discharge portion 223 to be accumulated in the waste liquid collection chamber 510. In the present embodiment, since the flows of the sheath liquid and the blood sample are a laminar flow, the blood sample is sucked into the aperture 231 and the blood sample passes through the aperture 231 while the blood sample is wrapped by the sheath liquid, and the blood sample flows into the second flow path 221.

As described above, since the blood sample flows while the blood sample is wrapped by the sheath liquid, the blood sample does not attach to the wall surfaces of the first flow path 211 and the second flow path 221 and the aperture 231, so that this can prevent contamination caused by the blood. Since the blood sample is caused to rapidly flow from the first flow path 211 into the aperture 231 having a smaller diameter, a change in the electric resistance is larger, and accordingly, a change in the blood cell pulse also becomes larger. As a result, a rose of the blood cell pulse and an S/N ratio can be improved. Since the blood sample is caused to flow into the aperture by using the sheath liquid, the blood sample passes through the center of the aperture, so that a stable blood pulse can be obtained.

Further, the blood sample having passed through the aperture 231 can be caused to flow to the downstream of the second flow path 221 in a stable manner, and therefore, the blood sample having passes through the aperture 231 can be prevented from recirculating to the aperture 231. Therefore, this can prevent a blood cell from being counted multiple times by mistake. The details of the flow of the sheath liquid and the blood sample in the flow cell 200 will be explained later. The control unit 900 causes a constant current to pass through the first electrode 216 and the second electrode 224, and the analysis unit 600 obtains blood cell pulses according to a change in the resistance value of the flow cell 200, and calculates the number of blood cells. The display unit 700 displays the number of blood cells calculated by the analysis unit 600.

As described above, the first electrode 216 is disposed in the first flow path 211 at a side opposite to the side where the blood sample flows into the first flow path 211 with respect to the aperture 231. The second electrode 224 is disposed in the second flow path 221 at a side opposite to the side where the blood sample and the sheath liquid flow out from the second flow path 221 with respect to the aperture 231. As described above, since the first electrode 216 and the second electrode 224 are disposed, the flows of the blood sample and the sheath liquid do not occur in proximity to the first electrode 216 and the second electrode 224 when an inter-electrode voltage is measured. Therefore, even in a case where bubbles generated by electrolysis are attaching to the first electrode 216 and the second electrode 224, there is no flow there around, and therefore, the baseline of the voltage of the blood cell pulse does not change, and the measurement can be performed in a stable manner. Large electrode sizes of the first electrode 216 and the second electrode 224 can be ensured, so that the measurement can be performed in a more stable manner.

Figure 4E:
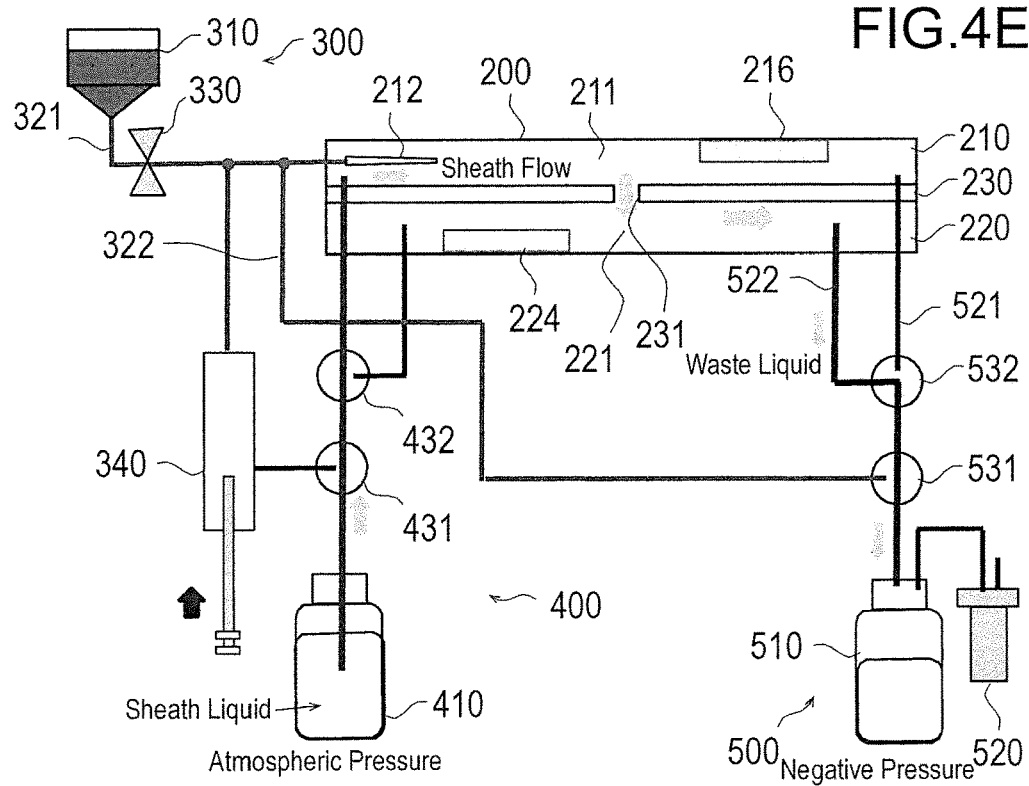
FIG. 4E is a schematic diagram connected subsequently to FIG. 4D.

Subsequently, the sheath liquid flows through the aperture 231 from the first flow path 211 to the second flow path 221 to perform cleaning (step S105). As shown in FIG. 4E, the control unit 900 provides the sheath liquid to the first flow path 211, and the sheath liquid flows through the aperture 231 from the first flow path 211 to the second flow path 221 to perform cleaning, and the waste liquid is collected. Therefore, bubbles and smears such as remaining blood (for example, protein) and the like attached to the inside of the first flow path 211, the inside of the second flow path 221, and the aperture 231 can be easily removed. As a result, this can prevent the baseline of the voltage of the blood cell pulse from changing due to bubbles attached to around the aperture 231, and the blood cell measurement can be performed in a stable manner. Electrolyzed water generated by electrolysis can also be removed. Therefore, the aperture 231 can maintain a clean state.

Figure 4F:
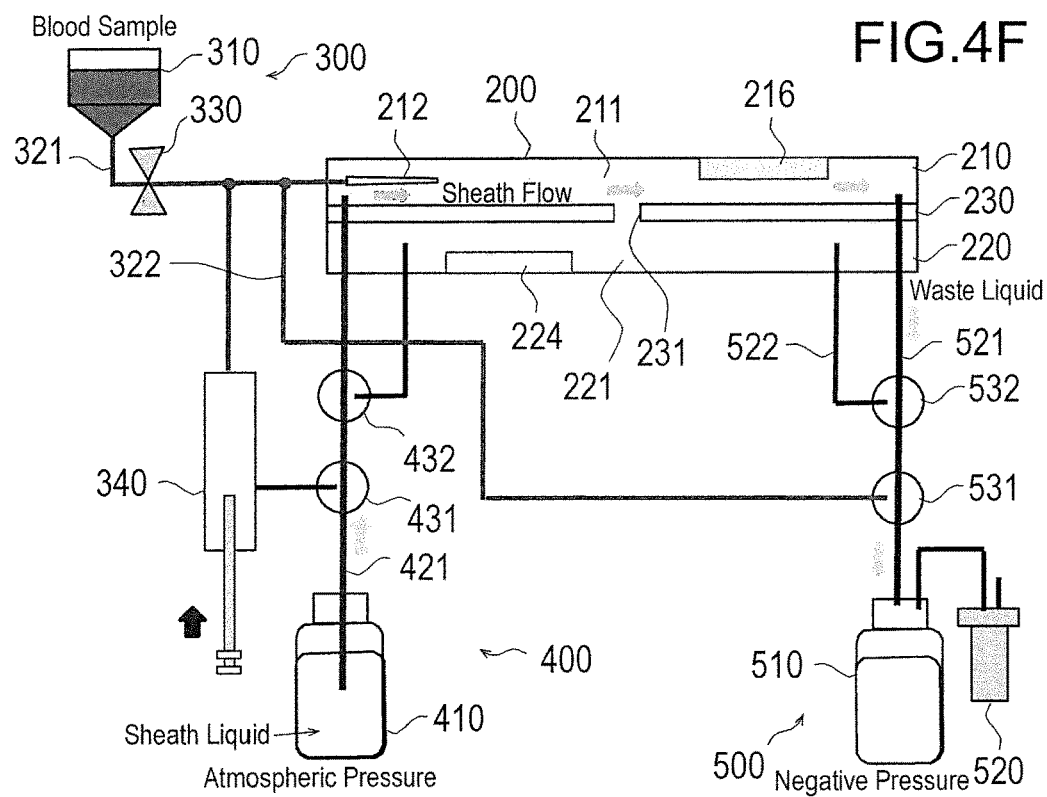
FIG. 4F is a schematic diagram connected subsequently to FIG. 4E.

Subsequently, the sheath liquid is caused to flow into the first flow path 211 to perform cleaning (step S106). As shown in FIG. 4F, the control unit 900 causes the sheath liquid to flow into the first flow path 211 to perform cleaning, and collects the waste liquid. Therefore, the sheath liquid passes through the first flow path 211 after the blood cells of the blood sample are measured, so that bubbles and smears such as remaining blood attached to the inside of the first flow path 211 can be removed.

Figure 4G:
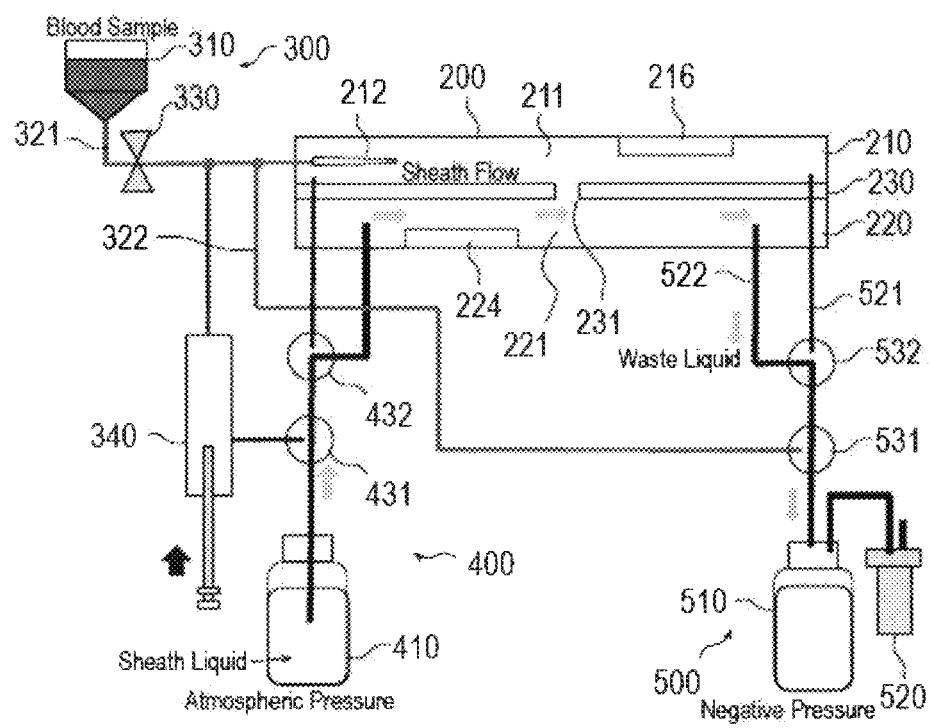
FIG. 4G is a schematic diagram connected subsequently to FIG. 4F.

Subsequently, the sheath liquid flows through the second flow path 221 to perform cleaning (step S107). As shown in FIG. 4G, the control unit 900 causes the sheath liquid to flow through the second flow path 221 to perform cleaning, so that the waste liquid is collected. Therefore, the sheath liquid is caused to pass through the second flow path 221 after the blood cells of the blood sample are measured, bubbles and smears such as remaining blood attached to the inside of the second flow path 221 can be removed.

As described above, in the present embodiment, the aperture 231 for connecting the first flow path 211 and the second flow path 221 in the middle thereof is disposed in the third layer between the first layer 210 having the first flow path 211 and the second layer 220 having the second flow path 221. The blood sample injected into the first flow path 211 flows to the aperture 231 while the blood sample is wrapped by the sheath liquid, and the blood sample changes its advancing direction into a substantially right angle, and the blood sample passes through the aperture 231. Then, after the blood sample passes through the aperture 231, the blood sample changes its advancing direction again into a substantially right angle, and the blood sample flows through the second flow path 221 toward the discharge portion 223 (see FIG. 4D). Hereinafter, a flow of blood sample in the flow cell 200 (hereinafter referred to as "sample flow") and a flow of sheath liquid (hereinafter referred to as "sheath flow") will be explained in details.

<Sample Flow and Sheath Flow in Flow Cell 200>

Figure 5:
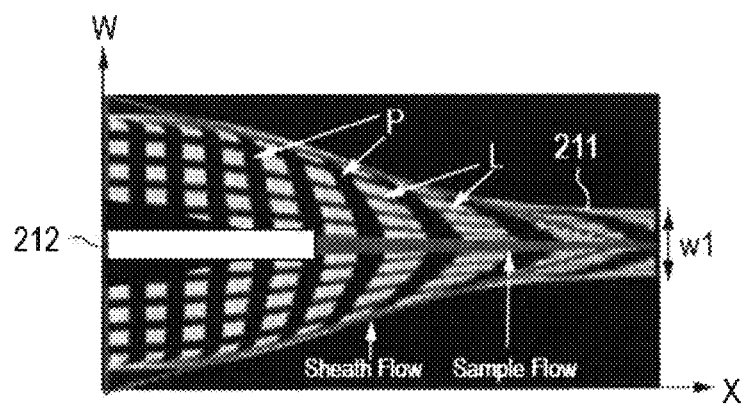
FIG. 5 is a schematic diagram illustrating, for example, a sample flow and a sheath flow around a sample injection portion in a case where it is seen from direction A of FIG. 2.

FIG. 5 is a schematic diagram illustrating, for example, the sample flow and the sheath flow around the sample injection portion 212 when it is seen from direction A of FIG. 2. In FIG. 5, L denotes a flow line of the sheath flow, and P denotes a flow velocity distribution of the sheath flow in the width direction (W direction) of the first flow path 211, i.e., a flow pattern of the sheath flow.

Figure 6A:
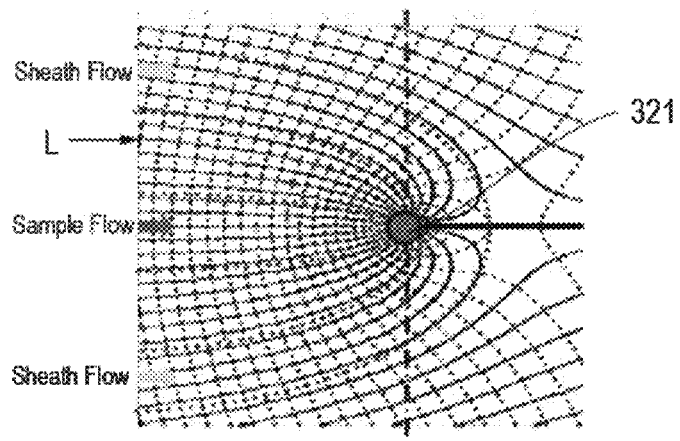
FIG. 6A is a schematic diagram illustrating the sample flow and the sheath flow around an aperture in a case where it is seen from direction A of FIG. 2.
Figure 6B:
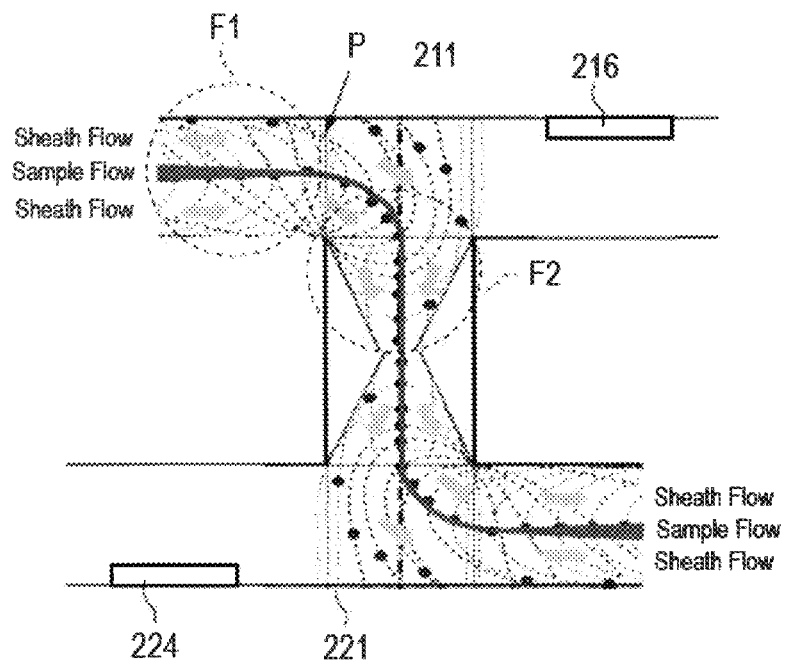
FIG. 6B is a schematic diagram illustrating the sample flow and the sheath flow around the aperture in a case where it is seen from direction W of FIG. 5.

FIG. 6A is a schematic diagram illustrating the sample flow and the sheath flow around the aperture 231 when it is seen from direction A of FIG. 2. FIG. 6B is a schematic diagram illustrating the sample flow and the sheath flow around the aperture 231 when it is seen from direction W of FIG. 5. L denotes flow lines of the sample flow and the sheath flow. P denotes flow patterns of the sample flow and the sheath flow.

As shown in FIG. 5, the sample flow and the sheath flow in the first flow path 211 are such that the speed increases as they advance to the downstream because the width of the first flow path 211 gradually decreases in the downstream direction (X direction). The flow lines of the sample flow and the sheath flow are denser at the downstream than at the upstream of the first flow path 211. However, since the sample flow and the sheath flow are a laminar flow, the flow lines do not cross each other.

The sample flow is gradually condensed as it advanced to the downstream due to the sheath flow (referred to as "fluid dynamics focusing (Flow Focusing)"). In the laminar flow, the layers of the flows do not mix with each other, and therefore, the sample flow is always located in the center of the sheath flow. Therefore, the blood cells in the blood sample flow mainly in the center of the aperture 231, and therefore, the analysis unit 600 can obtain blood cell pulses in a stable manner.

As shown in FIG. 6A, the sample flow and the sheath flow are a laminar flow, and therefore, the blood sample flows through the first flow path 211 while the blood sample is wrapped by the sheath liquid, and the blood sample is sucked into the aperture 231. By using the suction flow in the aperture 231, the blood cells wrapped by the sheath liquid can be caused to flow into the aperture 231 without any disturbance.

In general, whether a flow in a flow path becomes a laminar flow or a turbulent flow is known to be determined by Reynolds number $Re = u \cdot d / v$. In this case, u denotes a flow velocity, d denotes an internal diameter in the flow path, v denotes the coefficient of kinematic viscosity. In a case where the Reynolds number is equal to or less than about 2320, the flow becomes a laminar flow to be stable. Therefore, in a very small flow path such as the first flow path 211, the sample flow and the sheath flow are considered to be a laminar flow.

As shown in FIG. 6B, in the sample flow and the sheath flow, a viscous force is apparently more dominant than an inertial force, and therefore, it is considered that the advancing direction can be easily changed in a substantially right angle. The sample flow is further condensed in first and second fluid dynamics focusing areas F1, F2.

Modification

FIG. 7 is a schematic diagram illustrating a modification of the first embodiment. In the present modification, a particle analysis apparatus 101 includes a pressure pump 440 instead of the suction pump. The pressure pump 440 causes the inside of the sheath liquid chamber 410 to have a positive pressure, and pushes out and supplies the sheath liquid to the first flow path 211 or the second flow path 221. For example, in a case where the sheath liquid flows to the first flow path 211, the content (sheath liquid) in the sheath liquid chamber 410 is pressurized when the pressure pump 440 is activated. Since the inside of the waste liquid collection chamber 510 is at the atmospheric pressure, the sheath liquid in the sheath liquid chamber 410 is pushed out to the first flow path 211, the sheath liquid flows to the first flow path 211 to discharge from the discharge portion 215 so that the sheath liquid is accumulated in the waste liquid collection chamber 510.

Embodiment

A flow cell having a structure equivalent to the flow cell 200 according to the present embodiment was manufactured by way of experiment. The internal dimension of the first and second flow paths is 1 mm square. An aperture (φ0.1) for connecting a first flow path and a second flow path is formed in a third layer between a first layer and a second layer. By using a flow cell of such configuration, the blood sample and the sheath liquid are injected into the flow cell, and the flow was observed.

First, the first and second flow paths are filled with a sheath liquid. Then, the second collection valve is closed to block the downstream of the first flow path, and a path from the second flow path to a waste liquid collection chamber is established.

While the sheath liquid is injected from the sheath liquid injection portion, a blood sample is injected into the first flow path through a nozzle (φ0.25) of a sample injection portion. It was confirmed through observation that, in the first flow path, the sample flow is wrapped by the sheath flow to become a stable flow, and, as the flow path is narrowed, a flow focus is made by the sheath flow. The sample flow is located in the center of the sheath flow, and the sample flow changed its advancing direction into a substantially right angle while the sample flow is wrapped by the sheath flow, and the sample flow flowed into the penetration hole. It is considered that the sample flow and the sheath flow are further condensed by the aperture to be made into a flow in which the sample flow is located in the center.

The flow cell, the particle analysis apparatus, and the particle analysis method according to the present embodiment explained above achieve the following advantages.

According to the present embodiment, in the flow cell 200, the blood sample flows while the blood sample is wrapped by the sheath liquid, and the blood sample flows through the aperture 231. Since the blood sample does not flow around the first electrode 216 and the second electrode 224, the electrode is not contaminated by the blood sample. Since the blood sample and the sheath liquid do not flow around the first electrode 216 and the second electrode 224 during measurement of the blood cells, bubbles attached to the electrode is not detached by the flow, so that this can prevent a change in a baseline of the voltage of a blood cell pulse. Further, after the counting of the blood cells included in the blood sample is finished, smears and bubbles in the first flow path 211, the second flow path 221, and the aperture 231 in the flow cell 200 can be easily cleaned. Therefore, this can prevent or suppress contaminations and bubbles in the first flow path 211, the second flow path 221, and the aperture 231 in the flow cell 200 from affecting the accuracy of the blood cell count.

Second Embodiment

In the first embodiment, a case where a single aperture is provided between the first flow path and the second flow path has been explained. On the other hand, in the second embodiment, a case where apertures are provided between the first flow path and multiple other flow paths will be explained. In order to avoid repetition in explanation, the same configuration as the first embodiment will not be explained.

Figure 8A:
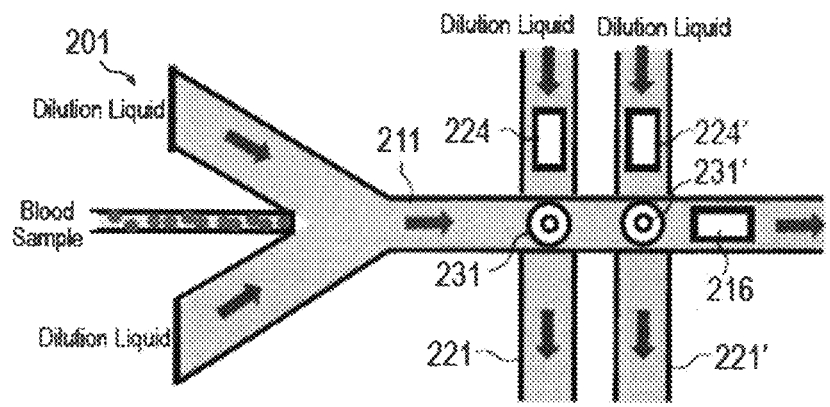
FIG. 8A is a schematic diagram illustrating, for example, an operation of a flow cell according to a second embodiment of the present subject matter.
Figure 8B:
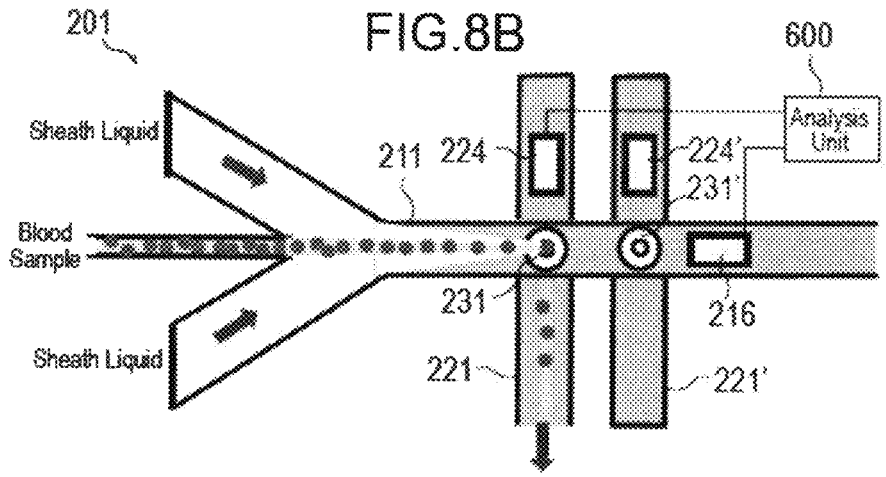
FIG. 8B is a schematic diagram connected subsequently to FIG. 8A.
Figure 8C:
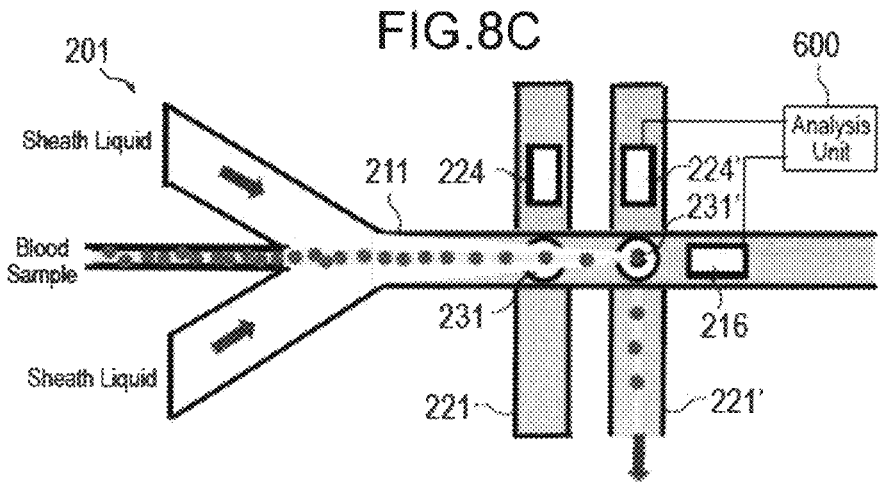
FIG. 8C is a schematic diagram connected subsequently to FIG. 8B.

FIG. 8A to FIG. 8C are schematic diagrams illustrating, for example, an operation of a flow cell according to the second embodiment. FIG. 8A to FIG. 8C illustrate, for example, a case where apertures are provided between a first flow path and a second flow path and between the first flow path and a third flow path.

As shown in FIG. 8A, in the present embodiment, the flow cell 201 includes not only the first flow path 211 and the second flow path 221 but also a third flow path 221'. In the third flow path 221', a third electrode 224' is disposed.

The third flow path 221' is preferably formed in the second layer 220 in which the second flow path 221 is formed. However, the embodiment is not limited to the case where the third flow path 221' is formed in the second layer 220. For example, the third flow path 221' may be disposed in another layer formed below the second layer 220.

The second flow path 221 and the third flow path 221' are preferably formed in a direction substantially perpendicular to the first flow path 211. However, the embodiment is not limited to the case where the second flow path 221 and the third flow path 221' are formed in a direction substantially perpendicular to the first flow path 211.

Hereinafter, for example, a case where the second flow path 221 and the third flow path 221' are formed in the second layer 220 in a direction substantially perpendicular to the first flow path 211 will be explained.

In the present embodiment, the third layer 230 includes not only the aperture 231 connecting the first flow path 211 and the second flow path 221 but also an aperture 231' (second connection hole) for connecting the first flow path 211 and the third flow path 221'. The aperture 231' has a size different from the aperture 231. For example, the aperture 231' may be formed to be larger than the aperture 231.

As shown in Table 1, in a blood cell measurement, a relationship between a size (diameter) of an aperture and a measurement range is known.

TABLE 1

| Diameter of aperture (μm) | Measurement range (μm) |
| --- | --- |
| φ30 | 0.6 to 18 |
| φ50 | 1 to 30 |
| φ100 | 2 to 60 |
| φ200 | 4 to 120 |

For example, hereinafter explained is a case where the aperture 231 and the aperture 231' are configured to have φ30 μm and φ50 μm, respectively, and leukocytes (about 10 μm), erythrocytes (about 6 μm), and platelets (about 2 μm) are counted.

When the measurement ranges of the apertures of φ30 μm and φ50 μm are referred in Table 1, both of the aperture 231 and the aperture 231' can be used for counting of leukocytes, erythrocytes, and platelets. However, from the perspective of attaining a higher measurement precision, i.e., improving the S/N ratio of the blood cell pulse, the aperture 231 is considered to be suitable for counting of the erythrocytes and platelets, and the aperture 231' is considered to be suitable for counting of the leukocytes.

A procedure for counting the erythrocytes, platelets and leukocytes by using the flow cell 201 is as follows.

First, as shown in FIG. 8A, a dilution liquid (sheath liquid) is provided to the first flow path 211, the second flow path 221, and the third flow path 221'.

Subsequently, as shown in FIG. 8B, the blood sample flowed from the first flow path 211 via the aperture 231 to the second flow path 221, and the erythrocytes and platelets are counted.

Subsequently, as shown in FIG. 8C, the blood sample flowed from the first flow path 211 via the aperture 231' to the third flow path 221', and the leukocytes are counted.

The diameter of the aperture of the erythrocytes (aperture 231) may be φ50 μm, and the diameter of the aperture of the platelets (aperture 231') may be φ30 μm.

As described above, apertures having different sizes are disposed in multiple flow paths, so that the blood cell count can be realized with a high precision, a small size, and at a low cost. FIG. 8A to FIG. 8C illustrate, for example, a case where there are two apertures. Alternatively, three or more aperture may be provided.

For example, a first aperture of φ30 μm may be provided between the first flow path and the second flow path. A second aperture of φ50 μm may be provided between the first flow path and the third flow path. A third aperture of φ100 μm may be provided between the first flow path and the fourth flow path. The first aperture is used for counting of the platelets, the second aperture is used for counting of the erythrocytes, and the third aperture is used for counting of the leukocytes. As described above, the platelets, erythrocytes, and leukocytes included in the blood sample can be caused to successively pass through the apertures having sizes suitable for each of them.

Blood cells may be counted by separately using a blood sample A for counting the erythrocytes and platelets and a blood sample B for counting the leukocytes. The blood sample A is diluted by a dilution liquid by, for example, 100 times. On the other hand, the blood sample B is diluted by the dilution liquid by, for example, 200 times, and thereafter, the blood sample B is hemolyzed with a hemolytic agent.

First, the blood sample A is supplied from the sample injection portion to the first flow path, and the counting is performed with an appropriate aperture, and thereafter, the blood sample A is discharged, and the inside of the flow cell 200 is cleaned.

Subsequently, the blood sample B is supplied from the sample injection portion to the first flow path, and the counting is performed with an appropriate detection, and thereafter, the blood sample B is discharged, and the inside of the flow cell 200 is cleaned.

As a result, it is not necessary to separately provide both of the flow cell for counting the erythrocytes and platelets and the flow cell for counting the leukocytes, and the counting can be performed with the same flow cell. Therefore the size of a particle analysis apparatus can be reduced.

Third Embodiment

In the first embodiment, a case where a single aperture is provided between the first layer and the second layer has been explained. On the other hand, in the third embodiment, a case where an aperture is provided between layers of three or more layers will be explained. In order to avoid repetition in explanation, the same configurations as those of the first embodiment will not be explained.

Figure 9A:
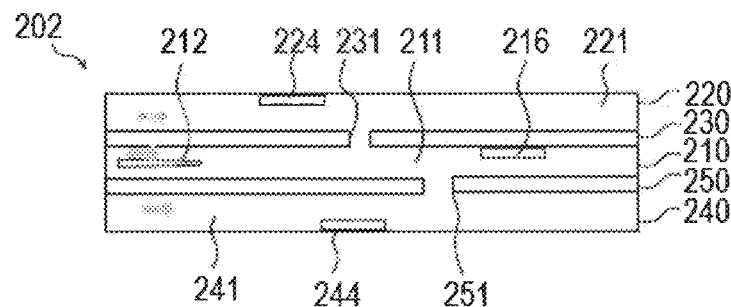
FIG. 9A is a schematic diagram illustrating, for example, an operation of a flow cell according to a third embodiment of the present subject matter.
Figure 9B:
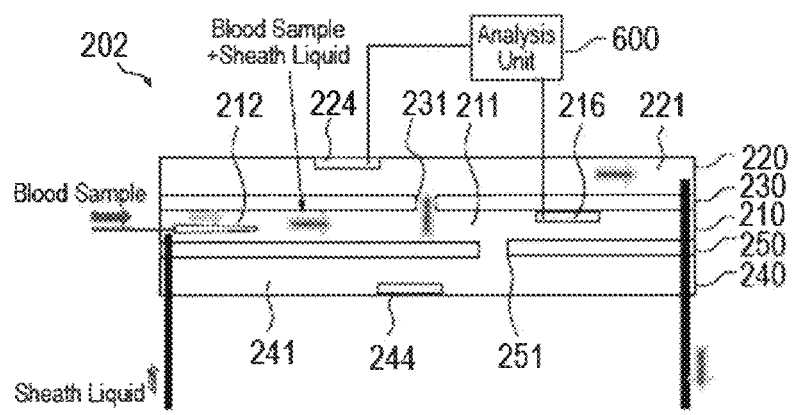
FIG. 9B is a schematic diagram connected subsequently to FIG. 9A.
Figure 9C:
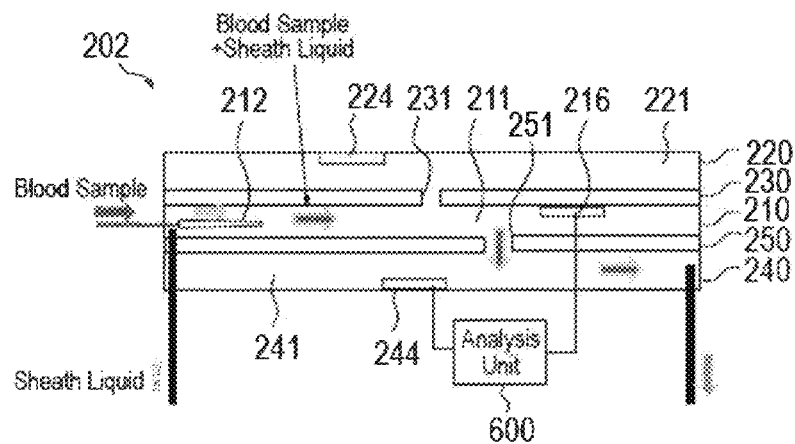
FIG. 9C is a schematic diagram connected subsequently to FIG. 9B.

FIG. 9A to FIG. 9C are schematic diagrams illustrating, for example, an operation of a flow cell according to the third embodiment. As shown in FIG. 9A, the flow cell 202 further includes a fourth layer 240 and a fifth layer 250 formed between the fourth layer 240 and the second layer 220.

In the present embodiment, the first electrode 216 is disposed at a side opposite to the side where the blood sample and the sheath liquid flow in from the first flow path 211 with respect to the aperture 231. The first electrode 216 is preferably disposed closer to the aperture 231 in the first flow path 211. The second electrode 224 is disposed in the second flow path 221 at a side opposite to the side where the blood sample and the sheath liquid flow out from the second flow path 221 with respect to the aperture 231. The second electrode 224 is preferably disposed closer to the aperture 231 in the second flow path 221.

The fourth layer 240 includes a third flow path 241 and a third electrode 244. When the recessed portion formed on the upper surface side of the fourth layer 240 and the lower surface of the fifth layer 250 are brought into contact with each other, the third flow path 241 is configured to have a rectangular cross section.

The fifth layer 250 includes an aperture 251 (second connection hole) connecting the second flow path 221 and the third flow path 241. The third electrode 244 is disposed at a side opposite to the side where the blood sample and the sheath liquid flow out from the third flow path 241 with respect to the aperture 251. The third electrode 244 is preferably disposed closer to the aperture 251 in the third flow path 241.

The aperture 251 has a size different from the aperture 231. For example, the aperture 251 is formed to be larger than the aperture 231. For example, the aperture 231 and the aperture 251 are configured to have φ30 μm and φ50 μm, respectively, and the erythrocytes and platelets of the blood sample are counted at the aperture 231, and the leukocytes are counted at the aperture 251.

When the blood cells in the blood sample are counted, a sheath liquid supply unit and a waste liquid collection unit, not shown, are controlled, and at a side where the sheath liquid flows out, the first to third flow paths 211, 221, and 241 are closed, and the first to third flow paths 211, 221, 241 are filled with the sheath liquid.

In a case where the blood cells are measured at the aperture 231 as shown in FIG. 9B, the second flow path 221 is opened and the first and third flow paths 211, 241 are closed at the side where the sheath liquid flows out, so that the blood sample and the sheath liquid are injected into the first flow path 211.

The blood sample injected into the first flow path 211 flows to the aperture 231 while the blood sample is wrapped by the sheath liquid, and the blood sample changes its advancing direction to a substantially right angle, i.e., an upward direction, and the blood sample passes through the aperture 231. When the blood sample passes through the aperture 231, the erythrocytes and platelets included in the blood sample are counted with the first electrode 216 and the second electrode 224. Then, the blood sample having passed through the aperture 231 changes its advancing direction to a substantially right angle again, and the blood sample flows through the second flow path 221, and the blood sample is collected by the waste liquid collection unit.

In a case where the blood cells are measured at the aperture 251 as shown in FIG. 9C, the third flow path 241 is opened and the first and second flow paths 211, 221 are closed at a side where the sheath liquid flows out, and the blood sample and the sheath liquid are injected into the second flow path 221.

The blood sample injected into the second flow path 221 flows to the aperture 251 while the blood sample is wrapped by the sheath liquid, and the blood sample changes its advancing direction to a substantially right angle at the aperture 251, and the blood sample passes through the aperture 251. When the blood sample passes through the aperture 251, the leukocytes included in the blood sample are counted with the first electrode 216 and the third electrode 244. Further, the blood sample passes through the aperture 251, and thereafter, the blood sample changes its advancing direction to a substantially right angle again, and the blood sample flows through the third flow path 241, and the blood sample is collected by the waste liquid collection unit.

As described above, the apertures having different sizes are disposed between multiple layers, so that the blood cell count can be realized with a high precision, a small size, and at a low cost.

As described above, in the embodiment, the particle analysis apparatus, and the particle analysis method according to the present subject matter have been explained. However, it is to be understood that a person skilled in the art can appropriately make an addition, a modification, and an omission to the present subject matter within the range of the technical gist.

For example, in the above first to third embodiments, the case where the number of blood cells included in the blood sample is measured has been shown as an example and explained. However, the particle analysis apparatus according to the present subject matter is not limited to measurement of the number of blood cells included in the blood sample, and the particle analysis apparatus according to the present subject matter can also be applied to counting of small particles having a particular size, for example, latex particles. Alternatively, a sensor may be provided in the flow cell 200 to allow measurement of the hemoglobin concentration.

The particle analysis apparatus according to the present subject matter may further include a heater, and the flow cell may have a laminated structure on the main body of the particle analysis apparatus, so that only the flow cell can be heated. When the flow cell is heated, the temperature of the sample flow and the sheath flow are stabilized, and the counting precision of the particles can be improved.

The first flow path, the second flow path, and the aperture may be formed in a single layer obtained by integrating the first layer, the second layer, and the third layer. The integration of the layers explained above can be made with a 3D printer.

What is claimed is:

1. A flow cell comprising:
a first layer having a first flow path and a first electrode;
a second layer having a second flow path and a second electrode; and
a third layer formed between the first layer and the second layer, and having a first connection hole connecting the first flow path and the second flow path,
wherein the first flow path has a first portion and a second portion arranged on opposing sides of the first connection hole, and the first electrode is disposed in the first portion of the first flow path and a sample is introduced to the first flow path in the second portion of the first flow path, and
wherein the second flow path has a third portion and a fourth portion arranged on opposing sides of the first connection hole, and the second electrode is disposed in the third portion of the second flow path and a fluid is discharged from the fourth portion of the second flow path.

2. The flow cell according to claim 1, wherein the second flow path is formed in parallel with the first flow path.

3. The flow cell according to claim 1, wherein the second layer further includes a third flow path,
the third layer further includes a second connection hole connecting the first flow path and the third flow path, and
the size of the first and the second connection hole is different.

4. The flow cell according to claim 2, further comprising:
a fourth layer having a third flow path; and
a fifth layer formed between the second layer and the fourth layer, and including a second connection hole connecting the second flow path and the third flow path,
wherein the size of the first and the second connection hole is different.

5. A particle analysis apparatus comprising:
a flow cell according to claim 1;
a sample supply unit supplying a sample having particles, which are to be counted, to the first flow path;
an analysis unit connected to the first electrode and the second electrode, and configured to analyze the particles, which are to be counted, on the basis of a resistance value between the first electrode and the second electrode.

6. The particle analysis apparatus according to claim 5, further comprising a sheath liquid supply unit supplying a sheath liquid to the first flow path and the second flow path.

7. The particle analysis apparatus according to claim 6, wherein a fluid injected from the sample injection portion flows through the first flow path while it is wrapped by the sheath liquid, and flows from the first flow path to the second flow path with a suction flow in the first connection hole.

8. A method of analyzing particle, the method comprising the steps of:
(a) supplying a sheath liquid from one end of a first flow path of a first layer and discharging the sheath liquid from the other end;
(b) supplying the sheath liquid from one end of a second flow path of a second layer and discharging the sheath liquid from the other end;
(c) closing the first flow path at a first side where the sheath liquid is discharged, closing the second flow path at a second side where the sheath liquid is supplied, supplying the sheath liquid to the first flow path, and discharging the sheath liquid via a first connection hole from the second flow path; and
(d) injecting a fluid to the first flow path at a third side where the sheath liquid is provided, and counting particles included in the fluid that passes through the first connection hole,
wherein the first connection hole is formed in a third layer between the first layer and the second layer, and connects the first flow path and the second flow path.

9. The method of claim 8, further comprising the steps of:
(e) causing the sheath liquid to flow through the first connection hole from the first flow path to the second flow path to perform cleaning;
(f) causing the sheath liquid to flow to the first flow path to perform cleaning; and
(g) causing the sheath liquid to flow to the second flow path to perform cleaning.

* * * * *